United States Patent [19]
Ideker et al.

[11] Patent Number: 6,122,553
[45] Date of Patent: Sep. 19, 2000

[54] METHOD AND APPARATUS FOR TREATING CARDIAC ARRHYTHMIA

[75] Inventors: Raymond E. Ideker, Birmingham, Ala.; Bruce H. KenKnight, Maple Grove, Minn.

[73] Assignee: UAB Research Foundation, Birmingham, Ala.

[21] Appl. No.: 09/393,857

[22] Filed: Sep. 9, 1999

Related U.S. Application Data

[62] Division of application No. 08/868,095, Jun. 3, 1997, Pat. No. 5,978,704.

[51] Int. Cl.$^7$ ...................................................... A61N 5/05
[52] U.S. Cl. ................................................................. 607/122
[58] Field of Search ..................... 607/119, 122, 607/123, 125

[56] References Cited

U.S. PATENT DOCUMENTS

| | | | |
|---|---|---|---|
| 3,825,015 | 7/1974 | Berkovits | 128/404 |
| 4,365,639 | 12/1982 | Goldreyer | 128/786 |
| 4,444,195 | 4/1984 | Gold | 128/642 |
| 4,567,901 | 2/1986 | Harris | 128/786 |
| 5,165,403 | 11/1992 | Mehra | 128/419 |
| 5,209,229 | 5/1993 | Gilli | 128/419 |
| 5,224,476 | 7/1993 | Ideker et al. | 128/419 D |
| 5,251,624 | 10/1993 | Bocek et al. | 607/6 |
| 5,292,338 | 3/1994 | Bardy | 607/5 |
| 5,304,139 | 4/1994 | Adams et al. | 607/122 |
| 5,314,430 | 5/1994 | Bardy | 607/5 |
| 5,395,373 | 3/1995 | Ayers | 607/8 |
| 5,403,351 | 4/1995 | Saksena | 607/4 |
| 5,403,354 | 4/1995 | Adams et al. | 607/5 |
| 5,405,375 | 4/1995 | Ayers et al. | 607/5 |
| 5,411,527 | 5/1995 | Alt | 607/5 |
| 5,423,772 | 6/1995 | Lurie et al. | 604/122 |
| 5,431,683 | 7/1995 | Bowald et al. | 607/5 |
| 5,433,729 | 7/1995 | Adams et al. | 607/5 |
| 5,456,706 | 10/1995 | Pless et al. | 607/122 |
| 5,476,499 | 12/1995 | Hirschberg | 607/123 |
| 5,978,704 | 11/1999 | Ideker et al. | 607/123 |

FOREIGN PATENT DOCUMENTS

| | | |
|---|---|---|
| 0 601 340 A1 | 6/1994 | European Pat. Off. . |
| WO 97/01373 | 1/1997 | WIPO . |

OTHER PUBLICATIONS

Feeser et al.; Strength–Duration and Probability of Success Curves for Defibrillation with Biphasic Waveforms, *Circulation*, 82(6):2128–2141 (1990).

Mark W. Kroll; A Minimal Model of the Monophasic Defibrillation Pulse, *Pace*, 16:769–777 (Apr., Part I 1993).

*Primary Examiner*—William E. Kamm
*Attorney, Agent, or Firm*—Myers Bigel Sibley & Sajovec

[57] ABSTRACT

An implantable system for the defibrillation or cardioversion of the atria and the ventricles of a patient's heart comprises: a first catheter configured for positioning in the right ventricle of the heart; a second catheter configured for positioning through the coronary sinus ostium and in the coronary sinus of the heart, with the first and second catheters together carrying at least three defibrillation electrodes; a power supply; and a control circuit operatively associated with the power supply and the electrodes. The control circuit is configured for delivering an atrial defibrillation pulse through at least two of the electrodes, or a ventricular defibrillation pulse through at least two of the electrodes.

3 Claims, 3 Drawing Sheets

METHOD AND APPARATUS FOR TREATING CARDIAC ARRHYTHMIA

This application is a divisional of U.S. patent application Ser. No. 08/868,095, filed Jun. 3, 1997, now, issued as U.S. Pat. No. 5,978,704.

FIELD OF THE INVENTION

The present invention relates to methods and apparatus for treating cardiac arrhythmia, and particularly relates to an implantable apparatus that can treat both atrial and ventricular arrythmia with the implantation of two transvenous leads.

BACKGROUND OF THE INVENTION

Atrial fibrillation is one of the most common cardiac arrhythmia. Health consequences associated with atrial fibrillation include decreased cardiac output, less regular ventricular rhythm, the formation of blood clots in the atrial appendages, and an increased incidence of stroke. While some drugs are available for the treatment of atrial fibrillation, they have a number of side effects which reduce their therapeutic utility.

Unlike patients afflicted with ventricular fibrillation, patients afflicted with atrial fibrillation are conscious. The pain associated with the administration of the defibrillation shock can be severe, and there is a need for means of carrying out atrial defibrillation in a manner that is less painful to the patient being treated. One means for reducing the pain associated with atrial defibrillation is to administer multiple shocks, but the administration of multiple shocks typically requires the implantation of additional electrodes.

For ventricular fibrillation, the patient is generally unconscious, the condition is life threatening, and the pain associated with shock is not an issue. It is, however, desirable to reduce the shock strength administered so that the size of the implantable device can be reduced, or to administer shocks in a manner that will decrease the likelihood of recurrence of fibrillation. To meet these objects, it is desirable to administer multiple shocks. Again, the administration of multiple shocks requires the implantation of additional electrodes.

Numerous patients are afflicted with both ventricular and atrial arrhythmias. For such patients, it would be exceedingly desirable to provide a single device that can carry out both atrial and ventricular defibrillation with minimum shock strength, and with minimal surgical intervention.

In view of the foregoing, a first object of the invention is to provide an implantable system for treating cardiac arrhythmia that does not require invasion of the chest cavity for the placement of epicardial electrodes.

A second object of the invention is to provide an implantable cardioversion system wherein the probability of successful cardioversion on administration of the first cardioversion pulse is enhanced, particularly in the case of ventricular fibrillation.

A third object of the invention is to provide an implantable system for treating cardiac arrhythmia that enables reduction of cardioversion, and particularly defibrillation, shock strength.

A fourth object of the present invention is to provide methods and apparatus for carrying out atrial defibrillation that will reduce the pain associated therewith.

A fifth object of the present invention is to provide methods and apparatus for carrying out atrial defibrillation that will reliably treat atrial fibrillation.

A sixth object of the present invention is to provide methods and apparatus for treating atrial fibrillation that minimizes the extent of the surgical intervention involved in implanting the necessary defibrillation electrodes, and minimizes the complexity involved in implanting the necessary defibrillation electrodes.

SUMMARY OF THE INVENTION

The foregoing and other objects and aspects of the present invention are described in greater detail in the drawings herein and the specification set forth below.

A first aspect of the present invention is an implantable system for the defibrillation or cardioversion of the atria and the ventricles of a patient's heart. The system comprises: a first catheter configured for positioning in the right ventricle of the heart; a second catheter configured for positioning through the coronary sinus ostium and in the coronary sinus of the heart, with the first and second catheters together carrying at least three defibrillation electrodes; a power supply; and a control circuit operatively associated with the power supply and the electrodes. The control circuit is configured for delivering an atrial defibrillation pulse through at least two of the electrodes, or a ventricular defibrillation pulse through at least two of the electrodes.

A second aspect of the present invention is an implantable system for the defibrillation or cardioversion of the atria and the ventricles of a patient's heart. The system comprises: a first catheter configured for positioning in the right ventricle of the heart; a second catheter configured for positioning through the coronary sinus ostium and in the coronary sinus of the heart, with the first and second catheters together carrying at least three defibrillation electrodes; a power supply; and a control circuit operatively associated with the power supply and the electrodes. The control circuit is configured for delivering an atrial defibrillation pulse through at least two of the electrodes, or a ventricular defibrillation pulse through at least two of the electrodes. The system includes a first and second pair of atrial defibrillation electrodes operatively associated with the control circuit and power supply, with the first pair of atrial defibrillation electrodes configured for delivering an atrial defibrillation pulse along a first current pathway and the second pair of atrial defibrillation electrodes configured for delivering a second defibrillation pulse along a second current pathway that is different from the first current pathway, and wherein the control circuit is configured for delivering an atrial defibrillation shock comprising in sequence the first and second atrial defibrillation pulses. Preferably, the system also includes a first and second pair of ventricular defibrillation electrodes operatively associated with the control circuit and the power supply, with the first pair of ventricular defibrillation electrodes configured for delivering a first ventricular defibrillation pulse along a first current pathway and the second pair of ventricular defibrillation electrodes configured for delivering a second defibrillation pulse along a second current pathway that is different from the first current pathway, and wherein the control circuit is configured for delivering a ventricular defibrillation shock comprising in sequence the first and second ventricular defibrillation pulses.

A third aspect of the present invention is an implantable system for the defibrillation or cardioversion of the atria and the ventricles of a patient's heart. The system comprises: a first catheter configured for positioning in the right ventricle of the heart; a second catheter configured for positioning through the coronary sinus ostium and in the coronary sinus of the heart; with the first and second catheters carrying at least three defibrillation electrodes, with the system including a plurality of primary electrodes configured for delivering a ventricular defibrillation pulse along a predetermined current pathway in a first portion of the heart, the current pathway defining a weak field area in a second portion of the heart, and with the defibrillation electrodes further including at least one auxiliary electrode configured for delivering an auxiliary pulse to the weak field area, with at least one auxiliary electrode configured for positioning through the coronary sinus and in a vein on the surface of the left ventricle of the heart; a power supply; and a control circuit operatively associated with the power supply and the electrodes. The control circuit is configured for delivering an atrial defibrillation pulse through at least two of the electrodes, or a cardioversion sequence comprising a monophasic auxiliary pulse through the auxiliary electrode and a biphasic defibrillation pulse through the primary electrodes. Preferably, the system also includes a first and second pair of atrial defibrillation electrodes, with the first pair of atrial defibrillation electrodes configured for delivering an atrial defibrillation pulse along a first current pathway and the second pair of atrial defibrillation electrodes configured for delivering a second defibrillation pulse along a second current pathway that is different from the first current pathway, and wherein the control circuit is configured for delivering an atrial defibrillation shock comprising in sequence the first and second atrial defibrillation pulses.

A fourth aspect of the present invention is a transvenous catheter for insertion into the heart of a patient, the catheter suitable for use in combination with a combination atrial and ventricular defibrillator. The catheter comprises an elongate lead flexibly configured for insertion down the superior vena cava of the heart, into the right atrium, through the opening of the coronary sinus, through the proximal and distal coronary sinus, and into a coronary vein on the surface of the left ventricle of the heart to achieve an operable configuration therein; a first defibrillation electrode connected to the lead; a second defibrillation electrode connected to the lead at a position distal to the first defibrillation electrode; and a third defibrillation electrode connected to the lead at a position distal to the second defibrillation electrode. The first, second, and third defibrillation electrodes spaced apart on the lead so that, when the catheter is in the operable configuration, the first defibrillation electrode is positioned in the proximal coronary sinus of the heart, the second defibrillation electrode is positioned in the distal coronary sinus or great cardiac vein of the heart, and the third defibrillation electrode is positioned in a coronary vein on the surface of the left ventricle of the heart.

DETAILED DESCRIPTION OF THE INVENTION

Figure 1:
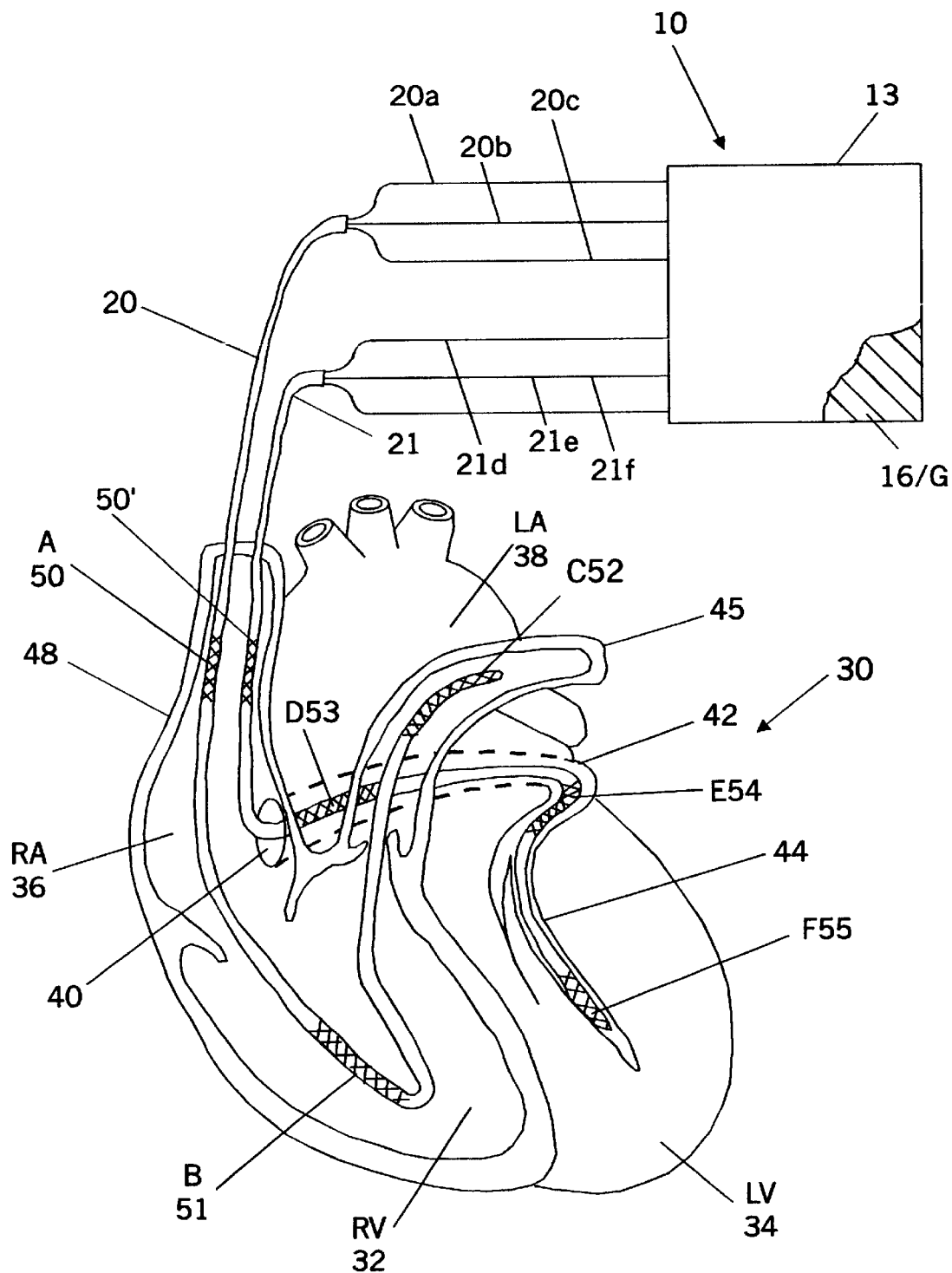
FIG. 1 illustrates a preferred set of electrode placements in an apparatus for carrying out the present invention.

The present invention may be used to treat all forms of cardiac tachyarrhythmias, including atrial and ventricular fibrillation, with defibrillation (including cardioversion) shocks or pulses. The treatment of polymorphic ventricular tachycardia, monomorphic ventricular tachycardia, ventricular fibrillation, and atrial fibrillation are particularly preferred.

Anatomically, the heart includes a fibrous skeleton, valves, the trunks of the aorta, the pulmonary artery, and the muscle masses of the cardiac chambers (i.e., right and left atria and right and left ventricles). The schematically illustrated portions of the heart 30 illustrated in FIG. 1 includes the right ventricle "RV" 32, the left ventricle "LV" 34, the right atrium "RA" 36, the left atrium "LA" 38, the superior vena cava 48, the coronary sinus "CS" 42, the great cardiac vein 44, the left pulmonary artery 45, and the coronary sinus ostium or "os" 40.

The driving force for the flow of blood in the heart comes from the active contraction of the cardiac muscle. This contraction can be detected as an electrical signal. The cardiac contraction is triggered by electrical impulses traveling in a wave propagation pattern which begins at the cells of the SA node and the surrounding atrial myocardial fibers, and then traveling into the atria and subsequently passing through the AV node and, after a slight delay, into the ventricles.

The beginning of a cardiac cycle is initiated by a P wave, which is normally a small positive wave in the body surface electrocardiogram. The P wave induces depolarization of the atria of the heart. The P wave is followed by a cardiac cycle portion which is substantially constant with a time constant on the order of 120 milliseconds ("ms").

The "QRS complex" of the cardiac cycle occurs after the substantially constant portion. The dominating feature of the QRS complex is the R wave which is a rapid positive or negative deflection. The R wave generally has an amplitude greater than any other wave of the cardiac cycle, and has a spiked shape of relatively short duration with a sharp rise, a peak amplitude, and a sharp decline. The R wave is the depolarization of the ventricles and therefore, as used herein, the term "ventricle activations" denotes R waves of the cardiac cycle. The QRS complex is completed by the S wave, which is typically a small deflection that returns the cardiac signal to baseline. Following the S wave, the T wave occurs after a delay of about 250 ms. The T wave is relatively long in duration (e.g., about 150 ms). The cardiac cycle between the S wave and the T wave is commonly referred to as the ST segment. The T wave is a sensitive part of the cardiac cycle, during which an atrial defibrillation shock is to be avoided, in order to reduce the possibility of an induced (and often fatal) ventricular fibrillation. The next cardiac cycle begins with the next P wave. The typical duration of a complete cardiac cycle is on the order of about 800 ms.

Various embodiments of the present invention can be illustrated with reference to FIG. 1. The defibrillator 10 of FIG. 1 includes an implantable housing 13 that contains a hermetically sealed electronic circuit 15 (see FIG. 2). The housing optionally, but preferably, includes an electrode comprising an active external portion 16 of the housing, with the housing 13 preferably implanted in the left thoracic region of the patient (e.g., subcutaneously, in the left pectoral region) in accordance with known techniques as described in G. Bardy, U.S. Pat. No. 5,292,338. The system includes a first catheter 20 and a second catheter 21, both of which are insertable into the heart (typically through the superior or inferior vena cava) without the need for surgical incision into the heart. The term "catheter" as used herein includes "stylet" and is also used interchangeably with the term "lead". Each of the catheters 20, 21 contains electrode leads wires 20a, 20b, 20c, 21d, 21e, and 21f, respectively, with the small case letter designation corresponding to the large-case letter designation for the defibrillation electrode to which each lead wire is electrically connected.

As illustrated in FIG. 1, the catheter 20 includes an electrode A; 50 that resides in the right atrium (the term "right atrium" herein including the superior vena cava and innominate vein), an electrode B; 51 positioned in the right ventricle (preferably in the right ventricular apex), and an electrode C; 52 positioned within the left pulmonary artery (the term "left pulmonary artery" herein includes the main pulmonary artery and the right ventricular outflow tract).

The second catheter 21 includes, from proximal to distal, a first electrode D; 53 positioned in the proximal coronary sinus, adjacent the coronary sinus ostium or "os" 40; a second electrode E; 55 positioned in the distal coronary sinus (preferably as far distal in the coronary sinus as possible) (the term "distal coronary sinus" herein includes the great cardiac vein); and a third electrode F; 56 at or adjacent the tip of the catheter in a coronary vein on the surface (preferably the posterolateral surface) of the left ventricle (e.g., in the lateral-apical left ventricular free wall). The position of electrode F may be achieved by first engaging the coronary sinus with a guiding catheter through which a conventional guidewire is passed. The tip of the torqueable guidewire is advanced under fluoroscopic guidance to the desired location. The lead 21 on which electrode F is mounted passes over the guidewire to the proper location. The guidewire is withdrawn and electrode F is incorporated into the defibrillation lead system.

Electrode A, 50 may optionally be positioned on lead 21 as electrode 50 and retain the same operable positions described above as when positioned on lead 20.

The active external portion of the housing 16 serves as an optional seventh electrode G, which may be used for either atrial or ventricular defibrillation.

The electrodes described in FIG. 1 and the specification above may, for convenience, be designated by the most adjacent structure. These structures are: the right atrium (RA), right ventricle (RV), pulmonary artery (PA) , coronary sinus ostium (OS) , distal coronary sinus (CS), and left ventricle (LV). Thus, when applied to electrodes the electrodes of FIG. 1:

RA means electrode A, 50;
RV means electrode B, 51;
PA means electrode C, 52;
OS means electrode D, 53;
CS means electrode E, 54; and
LV means electrode F, 55.

Figure 2:
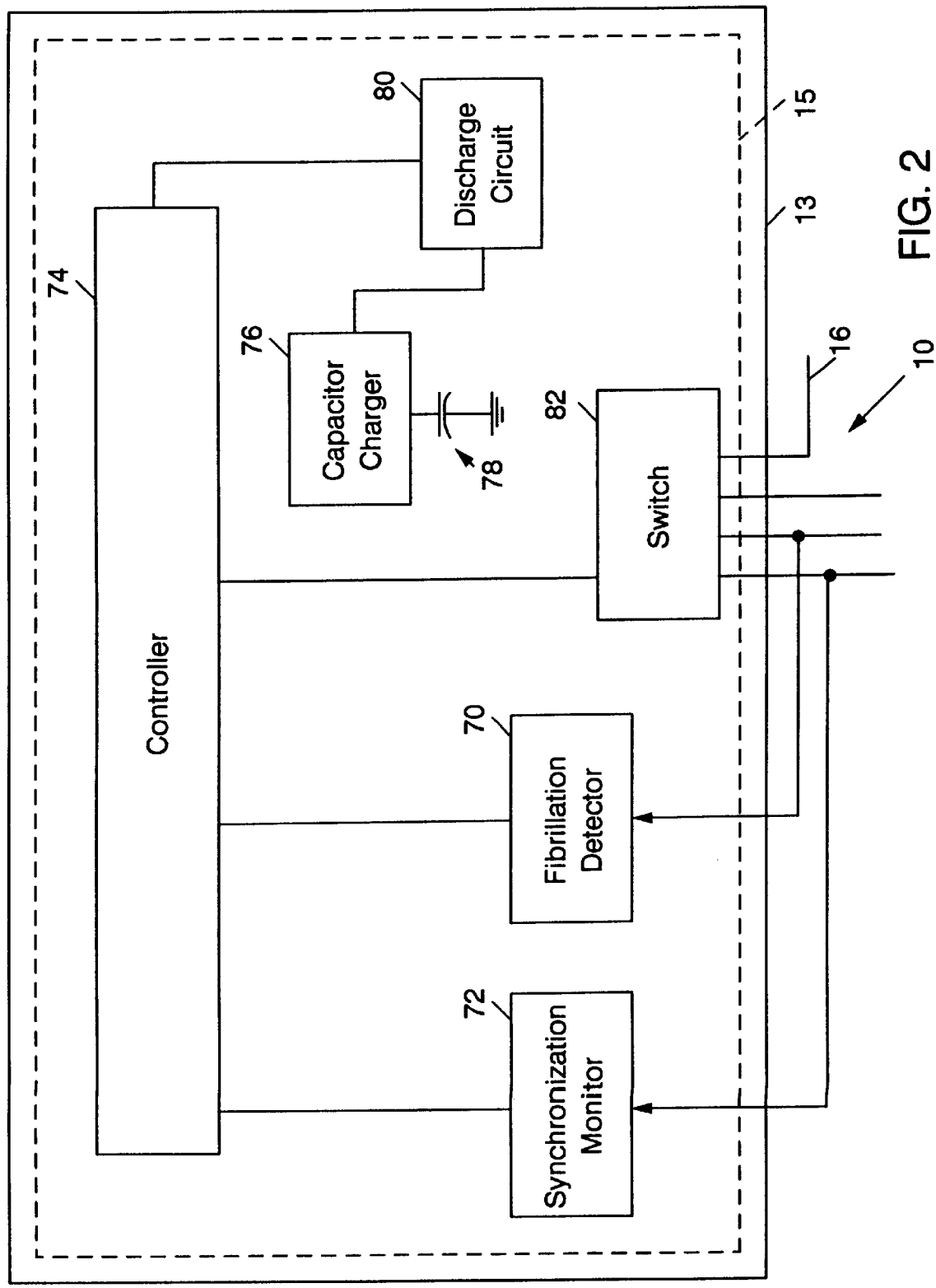
FIG. 2 schematically illustrates control circuitry employed in an apparatus of the present invention.

FIG. 2 illustrates one example of an implantable housing 13 containing an electronic circuit 15, which includes one or more amplifiers (not shown) for amplifying sensed cardiac signals. The amplified signals are analyzed by a atrial and ventricular fibrillation detector 70 which determines if ventricular fibrillation (or other arrhythmia, depending on the specific treatment for which the device is configured) is present. The detector 70 may be one of several known to those skilled in the art. As illustrated, a sensing signal may be provided by the electrode A 50, it will be appreciated by those of skill in the art that the sensing electrode may also be a plurality of sensing electrodes with a plurality of signals, such as bipolar configurations, and may also be electrodes that are positioned in alternate cardiac areas as is known in the art, such as for example, the CS. In this situation, the input line to the detector may be a plurality of lines which if providing only sensing will provide an input to the detector.

Ventricular sensing for timing the shocks for atrial defibrillation may be performed from the RV and/or LV electrodes.

The defibrillation electrodes may alternately be configured to sense cardiac cycles, or may have smaller sensing electrodes placed adjacent thereto and thereby provide input to the electronics package as well as provide a predetermined stimulation shock output to predetermined cardiac areas as directed by the controller.

The electronic circuit 15 also includes a cardiac cycle monitor ("synchronization monitor 72") for providing synchronization information to the controller 74. As discussed below, the synchronization is typically provided by sensing cardiac activity in the RV, but may also include other sensing electrodes which can be combined with the defibrillation electrodes or employed separately to provide additional assurance that defibrillation shock pulses are not delivered during sensitive portions of the cardiac cycle so as to reduce the possibility of inducing ventricular fibrillation.

Upon a signal from the detector 70, the controller 74, in turn, signals a capacitor charging circuit 76 which then charges the storage capacitor 78 to a predetermined voltage, typically from a battery source (not shown). The storage capacitor is typically 20 to 400 microfarads in size, and may be a single capacitor or a capacitor network (further, as discussed below, separate pulses can be driven by the same or different capacitors). The discharge of the capacitor is controlled by the controller 74 and/or a discharge circuit 80. The controller, based on information from the synchronization monitor 72, typically allows or directs the preselected shock pulse to be relayed to either a discharge circuit for further processing (i.e., to further shape the waveform signal, time the pulse, etc.) or directly to a switch. The controller may also control the proper selection of the predetermined defibrillation electrode pair(s), where multiple defibrillation electrodes are used, to direct the switch to electrically activate a desired electrode pair to align the predetermined electric shock pulse pathway through which the shock pulse is provided. As an alternative to a detector, the defibrillation pulses may be triggered by an external signal administered by a physician, with the physician monitoring the patient for the appropriate time of administration.

Numerous configurations of capacitor and control circuitry may be employed. The power supply may include a single capacitor, and the control circuit may be configured so that both the auxiliary pulse and the defibrillation pulse are generated by the discharge of the single capacitor. The power supply may include a first and second capacitor, with the control circuit configured so that the auxiliary pulse is generated by the discharge of the first capacitor and the defibrillation pulse is generated by the discharge of the second capacitor. In still another embodiment, the power supply includes a first and second capacitor, and the control circuit may be configured so that the auxiliary pulse is generated by the discharge (simultaneous or sequential) of both the first and second capacitors, and the defibrillation pulse likewise generated by the discharge of the first and second capacitors.

As illustrated by Table 1 below, numerous different combinations of electrodes from those shown in FIG. 1 may be employed to carry our atrial and ventricular defibrillation. In Table 1, polarity of electrode is illustrated by the direction of the arrows, but polarity is not critical and can be reversed. As will be seen from Table 1, a combination atrial and ventricular defibrillator may employ some or all of the electrodes illustrated in FIG. 1, and numerous combinations thereof.

TABLE 1

Electrode configurations.

|  | Ventricular Defibrillation | Atrial Defibrillation |
| --- | --- | --- |
| 1 | RA –> RV | RA –> CS |
| 2 | RA –> RV | PA –> OS |
| 3 | RA –> RV | RA –> OS |
| 4 | RA –> RV | OS –> CS |
| 5 | RA –> RV | CS –> PA |
| 6* | RA –> RV | PA –> RA |
| 7 | PA –> LV | RA –> CS |
| 8 | PA –> LV | PA –> OS |
| 9 | PA –> LV | RA –> OS |
| 10 | PA –> LV | OS –> CS |
| 11 | PA –> LV | CS –> PA |
| 12 | PA –> LV | PA –> RA |
| 13 | RA –> LV | RA –> CS |
| 14 | RA –> LV | PA –> OS |
| 15 | RA –> LV | RA –> OS |
| 16 | RA –> LV | OS –> CS |
| 17 | RA –> LV | CS –> PA |
| 18 | RA –> LV | PA –> RA |
| 19 | PA –> RV | RA –> CS |
| 20 | PA –> RV | PA –> OS |
| 21 | PA –> RV | RA –> OS |
| 22 | PA –> RV | OS –> CS |
| 23 | PA –> RV | CS –> PA |
| 24* | PA –> RV | PA –> RA |
| 25 | RV –> LV | RA –> CS |
| 26 | RV –> LV | PA –> OS |
| 27 | RV –> LV | RA –> CS |
| 28 | RV –> LV | OS –> CS |
| 29 | RV –> LV | CS –> PA |
| 30 | RV –> LV | PA –> RA |

Note that configurations 6 and 24, marked by an asterisk, employ Catheter A only.

Those skilled in the art will appreciate that still additional electrode combinations are possible for both atrial and ventricular defibrillation by employing the "active can" electrode G, 16, as discussed in greater detail below. In addition, multiple electrodes can be electrically coupled or "tied" together to form a single pole. For example, a shock can be delivered from either the RV or LV as one pole to the PA and OS tied together as the other pole.

Any suitable waveform may be used to carry out the present invention, including both monophasic and biphasic waveforms. Amplitude, polarity, and duration of waveforms are not critical and will be apparent to those skilled in the art, particularly in light of the further discussion below.

Figure 3:
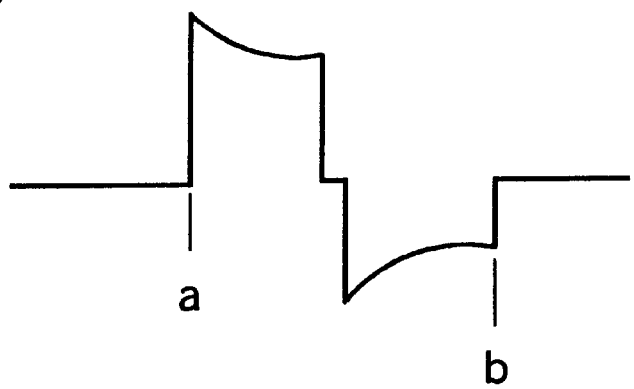
FIG. 3 illustrates a biphasic waveform that may be used to carry out atrial or ventricular defibrillation in accordance with the present invention.

For example, FIG. 3 illustrates a biphasic reverse exponential waveform that may be used to carry out atrial or ventricular defibrillation in accordance with the present invention, with the waveform being between time a and time b.

In a preferred embodiment of the invention, both atrial and ventricular defibrillation pulses are delivered along dual current pathways. Any combination of pathways among those set forth in Table 1 above may be employed. Particularly preferred current pathways employing the electrode configurations of FIG. 1 are set forth in Table 2 below.

TABLE 2

Dual current pathway electrode configurations.

|  | Ventricular Defibrillation | | Atrial Defibrillation | |
| --- | --- | --- | --- | --- |
|  | Pulse 1 | Pulse 2 | Pulse 1 | Pulse 2 |
| 1 | RV –> RA | LV –> PA | LV –> RA | RV –> PA |
| 2 | RV –> RA | LV –> PA | LV –> PA | RV –> RA |
| 3 | RV –> PA | LV –> RA | LV –> RA | RV –> PA |
| 4 | RV –> PA | LV –> RA | LV –> PA | RV –> RA |
| 5 | RV –> RA | LV –> PA | RA –> CS | PA –> OS |
| 6 | RV –> PA | LV –> RA | RA –> CS | PA –> OS |

As in Table 1 above, polarity of electrodes is illustrated by the direction of the arrows, but polarity is not critical and can be reversed. In addition in Table 2, the order of pulse 1 and pulse 2 may be switched, both for atrial defibrillation and ventricular defibrillation.

Figure 4:
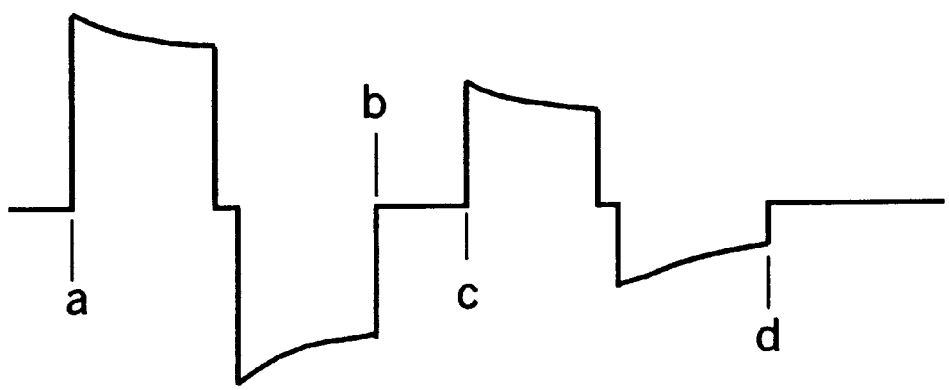
FIG. 4 illustrates first and second biphasic waveforms that may be used to carry out atrial or ventricular defibrillation along two current pathways in accordance with the present invention.

When dual current pathways are employed for the defibrillation shock, the waveform for each current pathway may be monophasic or biphasic. For example, FIG. 4 illustrates first and second reverse exponential biphasic waveforms that may be used to carry out atrial or ventricular defibrillation along two current pathways in accordance with the present invention. The first waveform of FIG. 4 is represented between time a and time b; the second waveform of FIG. 4 is represented between time c and time d. The time between the first and second waveforms (the time from time b to time c), will be apparent to those skilled in the art, but is preferably from 0 to 100 or 500 milliseconds, and more preferably from 0.1 to 50 milliseconds.

Figure 5:
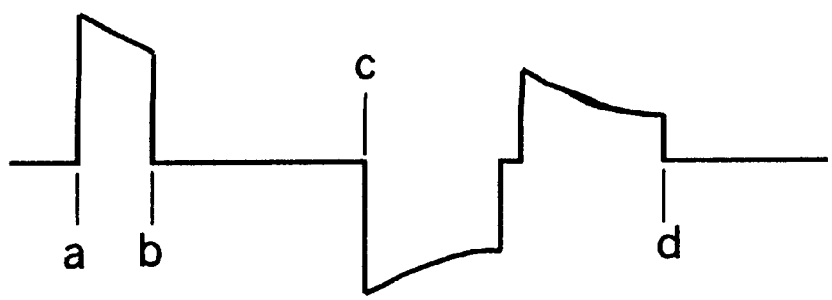
FIG. 5 illustrates a first auxiliary waveform and a second biphasic waveform that may be used to carry out atrial or ventricular defibrillation along two current pathways in accordance with the present invention.

As noted above, in a preferred embodiment of the present invention, a monophasic auxiliary waveform is delivered to a weak field area that is defined by the current pathway of the defibrillation waveform. FIG. 5 illustrates a first auxiliary waveform (from time a to time b) and a second reverse exponential biphasic waveform (from time c to time d) that may be used to carry out atrial or ventricular defibrillation along two current pathways in accordance with the present invention.

A. ATRIAL DEFIBRILLATION

In overview, an implantable system for the defibrillation of the atria of a patient's heart comprises (a) a first pair of atrial defibrillation electrodes configured for delivering a first atrial defibrillation pulse along a first current pathway in the heart; (b) a pulse generator operatively associated with the first pair of atrial defibrillation electrodes for delivering the first atrial defibrillation pulse; (c) a second pair of atrial defibrillation electrodes configured for delivering a second atrial defibrillation pulse along a second current pathway in the heart, with the second current pathway different from the first current pathway; and (d) a pulse generator operatively associated with the second pair of atrial defibrillation electrodes for sequentially delivering the second atrial defibrillation pulse after the first defibrillation pulse. The electrode pairs may be placed in a variety of different locations, as long as different current pathways for the first and second pulse are thereby achieved. A single electrode may participate in more than one electrode pair, so that, for example, two current pathways are achieved through three defibrillation electrodes. Additional electrodes may be tied together to one member of an electrode pair to provide a single pole, if so desired, and additional electrodes may be provided for following the first and second shocks with additional shocks.

In one embodiment of the invention, the first pair of atrial defibrillation electrodes comprises a defibrillation electrode positioned in the right atrium or superior vena cava of the heart, and a defibrillation electrode positioned in the distal coronary sinus or great cardiac vein of the heart. The electrodes themselves may be configured for positioning in the indicated location. Numerous alternatives for the second pair of atrial defibrillation electrodes forming a second pathway are possible. For example, the second pair of atrial defibrillation electrodes may comprise:

(A) a defibrillation electrode positioned in the proximal coronary sinus of the heart, and a defibrillation electrode positioned anterior to the left atrium of the heart (e.g., in the left pulmonary artery or on the external surface of a device implanted subcutaneously in the left thoracic region of the patient):

(B) a defibrillation electrode positioned in the left pulmonary artery the heart, and a defibrillation electrode positioned in the right ventricle of the heart;

(C) a defibrillation electrode positioned in the distal coronary sinus or great cardiac vein of the heart, and a defibrillation electrode positioned in the right ventricle of the heart;

(D) a defibrillation electrode positioned in the left pulmonary artery of the heart, and a defibrillation electrode positioned in the right atrium of the heart;

(E) a defibrillation electrode positioned in the left pulmonary artery of the heart, and a defibrillation electrode positioned in the distal coronary sinus or great cardiac vein of the heart (the electrode positioned in the distal coronary sinus or great cardiac vein may optionally be tied together with an electrode positioned in the right atrium as one pole);

(F) a defibrillation electrode positioned in the proximal coronary sinus of the heart, and a defibrillation electrode positioned in the right atrium of the heart; or (G) a defibrillation electrode positioned in the proximal coronary sinus of the heart, and a defibrillation electrode positioned in the distal coronary sinus or great cardiac vein of the heart (the electrode positioned in the distal coronary sinus or great cardiac vein may optionally be tied together with an electrode positioned in the right atrium as one pole).

Again, the electrodes may be configured for positioning in the indicated locations, and numerous variations on the foregoing will be readily apparent to those skilled in the art. For example, the first defibrillation pulse could be delivered by the second pair of electrodes indicated above, and the second defibrillation pulse could be delivered by the first pair of electrodes indicated above (in which case the indicated second pair of electrodes serves as the "first pair" and the indicated first pair serves as the "second pair"). In addition, multiple electrodes may be implanted to provide three, four, or five or more different alternative electrode pairs and current paths, and the electrode coupling to the pulse generator switched after implantation of the electrodes to optimize the electrode configuration for a particular patient.

As noted above, the instant invention provides two separate shock pulses to two separate current pathways determined by the electrode pair arrangement also as discussed above. Therefore, it will be appreciated by those of skill in the art that the capacitor 78 may be a single capacitor or a bank of parallel capacitors sufficiently charged and sized to be able to provide at least two separate shock pulses to predetermined electrodes positioned in the heart. Additionally, the capacitor 78 can be two or more separately charged capacitors (or bank of parallel capacitors) on separate lines to provide two separate and sequential shock pulses as controlled by the controller 74 and/or the discharge circuit 80. However, it is preferred that the capacitor 78 be a relatively large capacitor for insuring sufficient charge and decay period (i.e., long time constant and low, tilt) to provide sufficient energy for two shock pulses. For example, a capacitor with capacitance in the range of 200–1000 $\mu f$ or more, having an associated time constant in the range of 30 ms, would typically be charged to approximately 100–200 volts and would deliver a V(peak) in a typical first waveform of about 50–100 volts leading edge. If additional shocks beyond two are administered, then a larger capacitor may be employed. In the alternative wherein the electronic package employs a circuit to further shape the waveform, the capacitor may be charged to a higher voltage range (such as around 200 V).

In one embodiment of the invention, the pulse generator includes a single capacitor 78, and the controller 74 includes a switch (e.g., a crosspoint switch) operatively associated with that capacitor. The switch is configured to provide a biphasic pulse (i.e., a first phase of a pulse of a predetermined polarity followed by a second phase of a pulse of reversed polarity) as the first atrial defibrillation pulse and a biphasic pulse as the second atrial defibrillation pulse.

The controller 74 delivers a preselected electrical pulse to predetermined electrode pairs through a switch 82 which is preferably programmable. The capacitor charger 76, capacitor 78, controller 74, discharge circuit 80 and switch 82 thus form an electrical pulse generator. Therefore, it will be appreciated that in operation, in response to an input from the atrial fibrillation detector 70, the controller 74 controls the pulse generator to synchronize the delivery of the timed pulse output to the proper electrode pair in accordance with the cardiac cycle information received from the synchronization monitor 72 and the specific electrode configuration employed by the device. Further, when employing a biphasic waveform, it will be appreciated by those of skill in the art that the pulse generator also includes a crosspoint switch to switch the polarity of the electrode pair for delivery of the second (inverted or negative) waveform phase. It is also preferable that the electronic package include a receiver/transmitter coupled to the internal controller 74 for communicating with an external controller. Thus the pulse regimen could be altered by external input to the controller to alter for example, the waveform, the voltage, the electrode coupling, or even to retrieve data monitoring data received and stored in memory about the number of atrial fibrillation episodes and the effectiveness of the shock level.

In one embodiment of the invention, the switch 82 is programmable (e.g., by remote control such as by a radio signal) to alter the coupling of the pulse generator to the atrial defibrillation electrodes. This feature is advantageously employed when multiple electrodes are implanted so that the electrode pairs that deliver the first and second atrial defibrillation pulses may be changed to optimize the technique for a particular patient.

The energy of the first atrial defibrillation pulse is preferably not greater than 8 joules, more preferably not greater than 6 joules, still more preferably not greater than 4 joules, and most preferably not greater than 2 joules. The energy of the second atrial defibrillation pulse is typically not greater than the energy of the first defibrillation pulse (although such a result is possible where a dual capacitor design is employed), and is preferably not greater than 8 joules, more preferably not greater than 6 joules, still more preferably not greater than 4 joules, and most preferably not greater than 2 joules. The second atrial defibrillation pulse preferably follows the first atrial defibrillation pulse by 0 to 500 milliseconds, and more preferably follows the first atrial defibrillation pulse by 0 to 200 milliseconds. In the alternative, the second atrial defibrillation pulse may overlap the first atrial defibrillation pulse, for example by from one fourth to three fourths of the total shock duration (the duration of both shocks in series). The duration of each shock may be, for example, from three to twenty milliseconds, with total shock duration being, for example, from four and one half to forty milliseconds.

B. VENTRICULAR DEFIBRILLATION

One preferred embodiment of the foregoing apparatus is an implantable system for the defibrillation of the ventricles of the heart of a patient in need of such treatment. The system comprises a plurality of primary electrodes, at least one auxiliary electrode, a power supply, and a control circuit. The plurality of primary electrodes are configured for delivering a defibrillation pulse along a predetermined current pathway in a first portion of the heart, the current pathway defining a weak field area in a second portion of the heart. At least one auxiliary electrode is configured for delivering an auxiliary pulse to the weak field area, with the at least one auxiliary electrode configured for positioning through the coronary sinus and in a vein on the surface of the left ventricle of the heart. The control circuit is operatively associated with the primary electrodes, the at least one auxiliary electrode, and the power supply, the control circuit configured for delivering a cardioversion sequence comprising a monophasic auxiliary pulse through the auxiliary electrode, followed by a biphasic defibrillation pulse through the primary electrodes, with the defibrillation pulse delivered within 20 milliseconds after the auxiliary pulse, and with the first phase of the defibrillation pulse in opposite polarity to the auxiliary pulse.

The auxiliary pulse may be from 0.5 or 1 to 5 or 10 milliseconds in duration, with a 2 millisecond pulse currently preferred. The time interval from the end of the auxiliary pulse to the leading edge of the primary pulse may be from 1 or 2 milliseconds to 10, 15 or 20 milliseconds, with a delay of about 5 milliseconds currently preferred.

The optimal auxiliary-to-primary interval may differ depending on the type of rhythm or condition of the myocardial tissue at the time the therapy is applied. Therefore, the control circuitry may also be configured to sense a characteristic of the cardiac rhythm (e.g., an activation interval or a dynamical pattern of consecutive activation intervals) and then select an optimum auxiliary-to-primary shock time interval (e.g., from a look up table stored in a microprocessor memory).

In general, the control circuit is configured so that the auxiliary pulse is not more than 40% or 50% of the peak current and not more than 20% or 30% of the delivered energy (in Joules) of the defibrillation pulse. In a preferred embodiment, the trailing edge voltage of the auxiliary pulse is approximately or about equal to the leading edge voltage of the defibrillation pulse. Particular voltage, current, and energy outputs will depend upon factors such as the condition of the tissue and the particular disorder being treated. In general, the auxiliary pulse may have a peak voltage of from 20 or 30 volts to 200 or 250 volts, with a peak voltage range of 50 to 150 volts preferred. The energy of the auxiliary pulse may be from 0.01 or 0.5 to 1 or 2 Joules. The energy of the defibrillation pulse may be from 5 or 10 Joules to 30, 40 or 50 Joules.

C. GENERAL

Systems as described above may be implanted in a patient by conventional surgical techniques, or techniques readily apparent to skilled surgeons in light of the disclosure provided herein, to provide an implanted defibrillation or cardioversion system.

Additional features can also be added to the invention without affecting the function of the invention and result thereof. Such additional features include, but are not limited to, safety features such as noise suppression or multiple wave monitoring devices (R and T), verification checking to reduce false positive, precardioversion warning, programmed delayed intervention, bipolar configured sensing electrodes, intermittently activated defibrillation detector to reduce energy drain, a switching unit to minimize lines from the pulse generator, etc.

Although the system has been described above as an implantable system, it will be appreciated by those of ordinary skill in the art that the invention could also be incorporated into an external system which employs catheters to position the electrodes for a short time within a patient's heart.

The foregoing is illustrative of the present invention, and are not to be construed as limiting thereof. The invention is defined by the following claims, with equivalents of the claims to be included therein.

What is claimed is:

1. A transvenous catheter for insertion into the heart of patient, said catheter suitable for use in combination with a combination atrial and ventricular defibrillator, said catheter comprising:

An elongate lead flexibly configured for insertion down the superior vena cava of the heart, into the right atrium, through the opening of the coronary sinus, through the proximal and distal coronary sinus, and into a coronary vein on the surface of the left ventricle of the heart to achieve an operable configuration therein;

a first defibrillation electrode connected to said lead;

a second defibrillation electrode connected to said lead at a position distal to said first defibrillation electrode; and a third defibrillation electrode connected to said lead at a position distal to said second defibrillation electrode;

said first, second, and third defibrillation electrodes spaced apart on said lead so that, when said catheter is in said operable configuration, said first defibrillation electrode is positioned in the proximal coronary sinus of the heart;

said second defibrillation electrode is positioned in the distal coronary sinus or great cardiac vein of the heart; and said third defibrillation electrode is positioned in a coronary vein on the surface of the left ventricle of said heart.

2. A catheter according to claim 1, wherein said third defibrillation electrode is positioned at the distal tip of said lead.

3. A catheter according to claim 1, further comprising a fourth electrode connected to said lead at a position proximal to said first electrode so that, when said catheter is in said operable configuration, said fourth defibrillation electrode is positioned in the right atrium of the heart.

* * * * *